United States Patent [19]

Chakrabarti et al.

[11] 4,180,532

[45] Dec. 25, 1979

[54] PHOSPHORIC ACID ESTERS OF POLY(2-10)ETHYLENEOXY N BUTANE 1,4-DIOLS

[75] Inventors: Paritosh M. Chakrabarti; Mohammed M. Hashem, both of Wayne, N.J.

[73] Assignee: GAF Corporation, New York, N.Y.

[21] Appl. No.: 912,439

[22] Filed: Jun. 5, 1978

[51] Int. Cl.$^2$ .............................................. C07F 9/09
[52] U.S. Cl. .................................. 260/953; 260/929; 260/978; 260/980
[58] Field of Search ............................... 260/929, 953

[56] References Cited

U.S. PATENT DOCUMENTS

| 3,228,998 | 1/1966 | Fierce et al. ..................... 260/929 X |
| 3,275,667 | 9/1966 | Bohunek .......................... 260/929 X |

*Primary Examiner*—Anton H. Sutto

[57] ABSTRACT

Phosphoric acid esters of poly(2-10)ethyleneoxy n butane 1,4-diols are water soluble compounds which may be used in formulating light to heavy duty water-based metal working fluid compositions.

8 Claims, No Drawings

PHOSPHORIC ACID ESTERS OF POLY(2-10)ETHYLENEOXY N BUTANE 1,4-DIOLS

BACKGROUND OF THE INVENTION

The use of synthetic cutting fluid compositions has grown rapidly. The oil-free compositions are designed to impart lubricity at high temperatures, inhibit rust, reduce surface tension, produce low foam and be compatible with concentrated electrolyte solutions for hard water.

Examples of synthetic metal working fluid compositions which may be both oil and water soluble are those formed from conventional non-ionic surfactants which consist of a hydrophobe which has been polyoxyethylated. Such non-ionic surfactants have been provided with a phosphate radical which improves several of the sought for characteristics including increasing the hydrophilic characteristic of such surfactants. Examples of such metal working fluids are the ANTARA ® lubricant compositions which are sold by the GAF Corporation. These metal working fluid compositions are based on aliphatic and aromatic hydrophobic moieties which are further alkoxylated and phosphated.

The present invention provides compounds particularly suitable for use in formulating synthetic aqueous based metal working fluids. The compounds are phosphated, polyethoxylated (2-10 EO) n butane 1,4 diols. They are completely hydrophilic in nature. They do not contain any hydrophobic moiety. The particularly novel aspect of the present invention resides in phosphoric acid esters of the condensation products of one mole of butane-1,4-diol with from 2 to 10 moles of ethylene oxide. These esters are useful in a variety of applications such as synthetic aqueous based metal working fluids. Other uses are as lubricating additives, corrosion inhibitors, hydraulic fluids, flame retardant additives, plasticizers and the like. The phosphate esters of the present invention may be represented as follows:

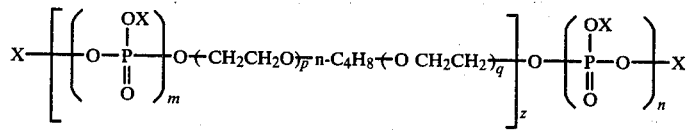

wherein X is a member selected from the group consisting of H and polyoxyethylbutanol having the general formula:

such that the compound can be either a mono-, di- or tri-ester of phosphoric or polyphosphoric acid, or mixtures of the three, m and n are positive integers of 1 or higher. In the case where m and n are greater than 1, their values are similar to the degree of polymerization occuring in polyphosphoric acid; q and p are positive integers the total of which is from 2 to 10 and wherein z is also an integer having a value of 1 or higher.

An examination of the general formula set forth above discloses a straight chain molecule which contains no branched chains. The component moieties of the compound are individually hydrophilic and in combination remain hydrophilic. This is believed to particularly distinguish the compounds of the present invention from those found generally available which are based on combinations of hydrophobic and hydrophilic moieties. The straight chain nature of the present compounds indicates a further characteristic that is particularly desirable that of being biodegradable. The compounds of the present invention may be further modified by forming ammonium, substituted ammonium, alkali metal or alkaline earth metal salts thereof.

The preparative methods for synthesizing the rather complex compounds and mixtures thereof of the invention follow well known synthetic procedures. The ethyoxylation is carried out by adding a pre-determined number of moles of ethylene oxide to the terminal hydroxyl groups of the butanediol. It is understood that this addition results in a well known random distribution of oxyethylene groups on either side of the butanediol moiety. The phosphation is also carried out by well known methods. The phosphating agent preferred in the present invention is polyphosphoric acid although $P_2O_5$ may also be used. The choice between the two phosphating agents depends upon whether a preponderance of diester or monoester is preferred. Polyphosphoric acid produces more monoester while $P_2O_5$ produces more diester.

Typical preparative methods used in the present invention were as follows:

n Butanediol is charged into a pressure vessel such as an autoclave. 0.05% NaOH catalyst based on the diol is added. A predetermined amount of ethylene oxide is charged into a cylinder which is coupled to the pressure vessel by means of a valved pipe. The valve is opened to permit the reaction to proceed at a pressure of 30 to 33 psig with the temperature controlled to 130° to 140° C. The reaction continues until the pressure drop indicates no unreacted ethylene oxide remains.

Phosphation of ethoxylated n butanediols may be carried out using $P_2O_5$ or polyphosphoric acid (PPA) of 115% strength. The phosphation was carried out in a four-necked flask which is equipped with a mechanical stirrer, a thermometer, an $N_2$ inlet (or $CaCl_2$ tube) and a vent tube (or a condenser). Prior to phosphation a color stabilizer may be added to the diol ethoxylate in amounts of 0.5 to 1 g. The stabilizer is hypophosphorous acid when $P_2O_5$ is used and sodium hypophosphite when PPA is used.

$P_2O_5$ is added in portions while holding the temperature to about 50°–60° C. Upon completion of the addition the reactants are heated for about five hours at 90°–95° C.

PPA in a predetermined amount is placed in a dropping funnel which was provided to one neck of the flask. The PPA was added dropwise maintaining the temperature at 40° to 45° C. Upon completion of the addition the reactants are heated for about two hours at 95° to 100° C.

The products of either phosphation may be bleached using 1 to 3 ml of 30% $H_2O_2$.

Typical preparations are shown below.

PREPARATIONS

| No. | Diol g., Moles | Phosphating Agent g., Moles | Temp. During Addition (Time of Add.) | Reaction Temp. (Time of Reaction) | Yield g. | % Monoester | % Diester |
|---|---|---|---|---|---|---|---|
| 1 | B1D.4EO 133, 0.5 | $P_2O_5$ 55, 0.37 | 50°–60° C. (30 min.) | 90°–95° C. (5 hrs.) | 188 | 44.5 | 65.4 |
| 2 | B1D.6EO 177, 0.5 | $P_2O_5$ 55, 0.37 | 60°–65° C. (30 min.) | 90°–95° C. (5 hrs.) | 232 | 41.0 | 50.0 |
| 3 | B1D.6EO 354, 1. | PPA 340, 2. | 50°–55° C. (25 min.) | 95°–100° C. (2 hrs.) | 694 | 71.9 | 13.4 |
| 4 | B1D.6EO 354, 1. | PPA 170, 1. | 40°–45° C. (30 min.) | 95°–100° C. (2 hrs.) | 524 | 47.8 | 11.1 |
| 5 | B1D.6EO 354, 1. | PPA 127, 0.75 | 40°–45° C. (20 min.) | 95°–100° C. (2 hrs.) | 481 | 49.0 | 0.0 |
| 6 | B1D.6EO 354, 1. | PPA 85, 0.5 | 40°–45° C. (20 min.) | 95°–100° C. (2 hrs.) | 439 | 35.6 | 3.1 |
| 7 | B1D.6EO 177, 0.5 | $P_2O_5$ 26, 0.185 | 60°–65° C. (20 min.) | 90°–95° C. (5 hrs.) | 232 | 45.4 | 45.7 |

The compounds of the present invention are all based on butanediol which for convenience sake will be indicated as B1D. The moles of ethylene oxide with which one mole B1D is ethyoxylated will be indicated as a number of EO and the phosphating agent will be indicated as $P_2O_5$ or PPA for polyphosphoric acid. The ratio shown following the butanediol, ethylene oxide and phosphating agent indicates the ratio between 1 mole of the ethoxylated butanediol and the moles of phosphating agent with which it has been reacted.

The compounds of the present invention are all based on B1D. The degree of ethoxylation varies between 2 EO to 10 EO, and the phosphation may be of varying degrees with either PPA or $P_2O_5$. The compounds falling within those described by such ratios are all suitable for use in synthetic metal working fluid compositions sometimes called coolants. When the compounds are diluted with water, they form true solutions. The compounds further produce little or no foam and such foam as may be produced is of a quick breaking character. The compounds of the invention further provide corrosion protection to most metals. They further stand up well under extreme pressure and elevated heat.

The desirable qualities of the ethoxylated phosphated butanediols of the present invention are demonstrated by comparison with two commercially available compounds used in preparing metal working fluid compositions. ANTARA ® LP-700 is a phosphate ester of phenol plus 6 EO reacted with one mole of $P_2O_5$ for each 2.7 moles of the ethoxylated phenol. ANTARA ® LK-500 is the phosphate ester of n $C_6H_{13}OH + 3.4$ EO and phosphated using 1 mole of $P_2O_5$ for each 2.7 moles of the ethoxylated alcohol.

The following tests are designed to demonstrate the foam characteristics of the compounds of the present invention and those of the two compounds used in commercial metal working fluids. A typical concentrate of aqueous based metal working fluid composition is the following:

| Compound | Concentrate |
|---|---|
| Phosphate ester | 10 Parts by Weight |
| Triethanol amine | 20 Parts by Weight |
| Water | 70 Parts by Weight |

The triethanol amine is used in the composition as an alkaline adjuster for the phosphate esters which are acidic. The commercially available metal working fluid compositions are also adjusted to alkaline in the same type of concentrate composition as the compounds of the present invention. In each of the runs shown later in Table I, 15 grams of the concentrate is diluted to 250 ml with distilled water resulting in approximately a 0.6 percent concentration of phosphate ester compound.

A mixer such as a Waring Blender is provided with a tape marked off in millimeters on the side of the mixing bowl. The ruled tape was adjusted so that the 0 mark coincided with the height of the unagitated dilute composition of metal working fluid. The solutions were stirred with the blender set at high speed for one minute. Readings of foam height were taken at the time the agitation was discontinued and at each succeeding minute until five minutes had elapsed.

TABLE I

BLENDER FOAM TEST
(15 g Concentrate Diluted to 250 ml With Distilled Water: 0.6% phosphate ester)

| PHOSPHATE ESTER (Neutralized as in Concentrate) | FOAM HEIGHT IN MM | | | | | |
|---|---|---|---|---|---|---|
| | 0 Min | 1 Min | 2 Min | 3 Min | 4 Min | 5 Min |
| Antara LP-700 (Nonbiodegradable) | 70 | 58 | 50 | 48 | 46 | 45 |
| Antara LK-500 (Biodegradable) | 112 | 105 | 90 | 85 | 68 | 58 |
| B1D.2EO:$P_2O_5$ (1:0.74) | 73 | 38 | 25 | 15 | 10 | 7 |
| B1D.4EO:$P_2O_5$ (1:0.74) | 70 | 40 | 26 | 18 | 15 | 8 |
| B1D.6EO:$P_2O_5$ (1:0.74) | 78 | 32 | 16 | 8 | 3 | 0 |
| B1D.6EO:$P_2O_5$ (1:0.37) | 83 | 53 | 35 | 21 | 13 | 8 |
| B1D.4EO:PPA* (A:1) | 52 | 24 | 9 | 7 | 6 | 5 |
| B1D.6EO:PPA* (1:0.5) | 72 | 23 | 7 | 0 | 0 | 0 |
| B1D.6EO:PPA* (1:0.75) | 71 | 25 | 1 | 0 | 0 | 0 |
| B1D.6EO:PPA* (1:1) | 70 | 24 | 9 | 0 | 0 | 0 |
| B1D.6EO:PPA* (1:1.5) | 63 | 26 | 7 | 0 | 0 | 0 |
| B1D.6EO:PPA* (1:2) | 52 | 12 | 1 | 0 | 0 | 0 |

*115% PPA

It is to be noted that all of the above metal working fluid compositions are biodegradable with the exception of ANTARA ® LP-700. Biodegradability is a most desirable feature in metal working fluid compositions particularly with the raised awareness with respect to safeguarding the enviornment from unnecessarily contaminated effluents.

It is to be noted that all of the metal working fluid compositions based on ethoxylated, phosphated butanediols produce less foam than biodegradable alkoxylated phosphated alcohols, a foam which breaks more rapidly than either commercial product. The decrease in foam production and the relatively quick breaking of that produced, increases with the degree of ethoxylation. The compositions are further improved when the phosphating agent is PPA which produces a preponderance of monoester. The outstanding compound with respect to low foam is B1D.6EO:PPA (1:1). It was incorporated in compositions having various ratios with respect to triethanolamine and water and the pH noted. The compositions are set forth in Table II. The parts shown there are by weight.

Compositions A, B and C are shown in Table II.

TABLE II

|  | Composition A | Composition B | Composition C |
|---|---|---|---|
| B1D.6EO:PPA (1:1) | 10 Parts | 10 Parts | 5 Parts |
| Triethanolamine | 20 Parts | 33.5 Parts | 20 Parts |
| Water | 70 Parts | 56.5 Parts | 75 Parts |
| pH | 8.25 | 8.6 | 8.5 |

The compositions were diluted in water to a concentration of 0.6 percent phosphate ester. This required formulation C to be added in twice the amount as A and B to 250 ml. The results of the foam test are shown in Table III.

TABLE III

BLENDER FOAM TEST
(Compositions of Table II, Diluted to 0.6% Phosphate Ester Conc. with Distilled Water)

| COMPOSITIONS | FOAM HEIGHT IN MM | | | | | |
|---|---|---|---|---|---|---|
|  | 0 Min | 1 Min | 2 Min | 3 Min | 4 Min | 5 Min |
| A | 70 | 25 | 8 | 0 | 0 | 0 |
| B | 70 | 35 | 14 | 0 | 0 | 0 |
| C | 70 | 27 | 3 | 0 | 0 | 0 |

The results indicate that the phosphate esters of the current invention have fast breaking foam irrespective of the degree of neutralization. It is noted that no foam remained at the end of three minutes.

Further reductions in foam and increase in the speed of breaking thereof were obtained by adding to 99% by weight of composition C 1% by weight of Surfynol 104E (tetramethyl decynediol in ethylene glycol 50% concentration). The compositions C and C plus Surfynol 104E were agitated in the blender at a 0.6 percent phosphate ester concentration with the following results:

TABLE IV

BLENDER FOAM TEST
(Compositions Diluted with Distilled Water to 250 ml and 0.6%)

| COMPOSITIONS | FOAM HEIGHT IN mm | | | | | |
|---|---|---|---|---|---|---|
|  | 0 Min | 1 Min | 2 Min | 3 Min | 4 Min | 5 Min |
| C | 70 | 27 | 3 | 0 | 0 | 0 |
| C with Surfynal 104E | 25 | 1 | 0 | 0 | 0 | 0 |

The lubricating properties of compounds of the present invention were measured in aqueous solution for wear protection be means of a standard Four Ball test and by the extreme pressure lubricating properties as measured by the Falex text.

The Four Ball test is carried out with a test load of 100 kg at 1500 rpm at an initial temperature of 100° F. for five minutes. One half inch diameter chrome alloy steel balls were used. Three balls are held stationary abutting one another below the fourth ball which is urged against the others at the load indicated, turning at the indicated speed while immersed in the various aqueous based metal working fluid compositions to be tested. The test was run for five minutes after which the balls were retrieved and examined for wear. The smaller the scar, the more effective compound tested.

The metal working composition for the purposes of carrying out the Four Ball wear test was prepared by diluting 12½ grams of the stock compositions into sufficient water to 250 ml of solution. The resultant composition has a phosphate ester compound concentration of 0.5%. An adjustment was made in the total amount of triethanolamine present in the test solution in that the pH of each sample was adjusted to a consistent $8.3 \pm 0.1$. The results of the test is shown in Table V. It will be seen that the compounds of the present invention give results comparable to the leading commercial product.

TABLE V

SHELL FOUR BALL WEAR TEST
(0.5% Phosphate Ester-pH to $8.3 \pm 0.1$ with TEA)

| PHOSPHATE ESTER | WEAR SCAR DIAMETER |
|---|---|
| Water only to pH 8.3 with TEA | Failure[1] |
| Antara LP-700 | 0.77 |
| B1D.2EO:$P_2O_5$ (1:0.74) | 0.74 |
| B3D.2EO:$P_2O_5$ (1:0.74) | 0.79 |
| B1D.4EO:$P_2O_5$ (1:0.74) | 0.85 |
| B2D.4EO:$P_2O_5$ (1:0.74) | 0.76 |
| B3D.4EO:$P_2O_5$ (1:0.74) | 0.79 |
| B1D.6EO:$P_2O_5$ (1:0.74) | 0.78 |
| B2D.6EO:$P_2O_5$ (1:0.74) | 0.76 |
| B3D.6EO:$P_2O_5$ (1:0.74) | 0.74 |
| B1D.6EO:PPA[2] (1:0.5) | 0.77 |
| B1D.6EO:PPA[2] (1:2) | 0.76 |

[1]Failure means, the rpm could not be maintained and the test had to be abandoned before the required 5 minutes were over. A typical scar diameter at failure (Less than 5 min.) is well over 3 mm.
[2]115% PPA.

A Four Ball wear test was carried out comparing the preferred compound of the present invention B1D.6EO:PPA (1:1) was compared with a 0.5% solution of triethanolamine and the leading commercially available product ANTARA® LP-700. The other variable included in this particular test was the diluting of succeeding compositions by a half from the preceeding one in order to determine at what point the composition was no longer sufficiently effective to prevent undue wear. The results of this test are set forth in Table VI which follows.

TABLE VI

FOUR BALL WEAR TEST
(pH of Test Solutions $8.3 \pm 0.1$)

| COMPOSITION/ CONCENTRATION | SCAR DIAMETER (mm) | | | | | |
|---|---|---|---|---|---|---|
|  | 1.0% | 0.5% | 0.25% | 0.125% | 0.062% | 0.031% |
| Water alone (pH 8.3 with TEA) |  |  |  | FAILURE[1] |  |  |
| 0.5% Solution of TEA (pH-10.1) |  |  |  | FAILURE[1] |  |  |

TABLE VI-continued

FOUR BALL WEAR TEST
(pH of Test Solutions 8.3 ± 0.1)

| COMPOSITION/ | SCAR DIAMETER (mm) | | | | | |
|---|---|---|---|---|---|---|
| CONCENTRATION | 1.0% | 0.5% | 0.25% | 0.125% | 0.062% | 0.031% |
| Antara LP-700 | 0.75 | 0.77 | 0.80 | 1.42 | Failure[1] | Failure[1] |
| B1D.6EO:PPA[2](1:) | 0.77 | 0.77 | 0.76 | 0.86 | 0.92 | 2.46 |

[1] For definition see footnote of Table V.
[2] 115% PPA.

Some of the compositions described in Table I are diluted to give a 0.15% of the phosphate ester compound in test solution. No adjustment of the pH after dilution was attempted. The results of the load bearing capacity tests are shown in Table VII below.

TABLE VII

FALEX LOAD-BEARING CAPACITY TEST
(Compositions Diluted to Give 0.15%
Phosphate Ester Compound)

| COMPOUND TESTED (0.15% Concentration) | JAW LOAD MAX = FAILURE PRESSURE (lbs.) | TORQUE LBS/INCH |
|---|---|---|
| Water alone | — | — |
| Antara LP-700 | 2200 | 66 |
| B1D.2EO:P$_2$O$_5$ (1:0.74) | 1900 | 70 |
| B1D.4EO:P$_2$O$_5$ (1:0.74) | 2000 | 70 |
| B2D.4EO:P$_2$O$_5$ (1:0.74) | 2000 | 70 |
| B3D.4EO:P$_2$O$_5$ (1:0.74) | 1800 | 70 |
| B1D.6EO:P$_2$O$_5$ (1:0.74) | 2000 | 72 |
| B2D.6EO:P$_2$O$_5$ (1:0.74) | 1800 | 72 |
| B3D.6EO:P$_2$O$_5$ (1:0.74) | 1800 | 72 |
| B1D.6EO:PPA* (1:0.5) | 1900 | 74 |
| B1D.6EO:PPA (1:1) | 2500 | 74 |

*115% PPA

A second series of load bearing capacity tests were carried out comparing the preferred compound of the present invention, B1D.6EO:PPA (1:1) with a leading commercial compound ANTARA® LP-700. The comparisons are made at three different concentrations of the metal working fluid composition. The results are shown in Table VIII.

TABLE VIII

FALEX LOAD CARRYING CAPACITY TEST
(pH of Test Solutions 8.3 + 1)

| CONCENTRATION/ COMPOUND | JAW LOAD, MAX = FAILURE PRESSURE (lbs.) | TORQUE LBS/INCH |
|---|---|---|
| 0.15% | | |
| Antara LP-700 | 2400 | 63 |
| B1D.6EO:PPA* (1:1) | 2500 | 73 |
| 0.075% | | |
| Antara LP-700 | 1500 | 60 |
| B1D.6EO:PPA* (1:1) | 1800 | 65 |
| 0.037% | | |
| Antara LP-700 | 800 | — |
| B1D.6EO:PPA (1:1) | 1800 | 65 |

*115% PPA

Comparison of results between the commercial product and the preferred compound of the present invention show near equivalence at 0.15% concentration but a longer continued effectiveness at diminishing concentrations by the preferred compound of the present invention.

The same two compounds, the preferred phosphate ester of the present invention and ANTARA® LP-700 were tested for rust inhibition. The materials used were cast iron blocks, 2½×5×¾". They were freshly polished with aluminum oxide paper of 240 grit to remove any oxides from the surface. The blocks were further cleaned with mineral spirits or hexane and wiped with a clean cloth till no black oxide appeared on the cloth.

Test solutions were applied as relatively uniform drops usually in a row of five across the face of the block. The test blocks were left undisturbed for 24 hours at ambient temperature. During this time all the water in the metal working fluid evaporates. Then the block may be examined for rust. The outlines of the dried solution are visible and an estimate of rust inhibition is made by averaging the areas of each spot which show rust.

ANTARA® LP-700 was compared with water alone and the preferred compound of the present invention. The test solutions were adjusted to a pH of 8.3±0.1 with triethanolamine. The results were rated on a scale of A through E. A equals no rust. B less than 10% of the area on which the compositions were allowed to dry are covered by rust. C between 10 to 50% are covered by rust. D between 50 and 99% are covered by rust. E 100% covered by rust.

The compositions are shown at either 0.1 or 0.3 concentration. One set of runs included 0.02% sodium nitrite and another 0.06% sodium nitrite as a supplementary rust inhibitor. Results are shown in Table XI.

TABLE IX

RUST INHIBITION TEST
(Test Solution Adjusted to pH 8.3 + 0.1 with TEA)

| COMPOUND | CONCENTRATION IN TEST SOL'N | | AVERAGE RUST RATING* |
|---|---|---|---|
| | % COMPOUND | % NANO$_2$ | |
| Water Alone | — | None | E |
| Antara LP-700 | 0.1 | None | B |
| B1D.6EO:PPA (1:1) | 0.1 | None | B |
| Antara LP-700 | 0.3 | None | A |
| B1D.6EO:PPA (1:1) | 0.3 | None | A |
| Antara LP-700 | 0.1 | 0.02 | A |
| B1D.6EO:PPA (1:1) | 0.1 | 0.02 | A |
| Antara LP-700 | 0.1 | 0.06 | A |
| B1D.6EO:PPA (1:1) | 0.1 | 0.06 | A |

The results show that the preferred compound of present invention itself exhibits rust inhibitory properties and that these properties can be enhanced by the addition of a supplementary rust inhibitor.

The compounds of the present invention have been shown to have rust inhibiting properties. They are compatible with electrolyte corrosion inhibitors commonly added to metal working fluid compositions such as sodium nitrite. Load bearing tests were run comparing the preferred compound of the present invention and a leading commercial product ANTARA® LP-700 in compositions containing NaNO$_2$. The results are shown in Table X.

TABLE X

FALEX LOAD BEARING CAPACITY TEST
(In the Presence of NaNO$_2$) pH of Test Solution: 8.3 + 0.1

| COMPOUND | CONCEN-TRATION % | NaNO$_2$ | JAW LOAD, MAX. = FAILURE PRESSURE (lbs) |
| --- | --- | --- | --- |
| Antara LP-700 | 0.15 | 0.03 | 1300 |
| B1D.6EO:PPA* (1:1) | 0.15 | 0.03 | 1900 |
| Antara LP-700 | 0.075 | 0.015 | 1200 |
| B1D.6EO:PPA* (1:1) | 0.075 | 0.015 | 1600 |
| Antara LP-700 | 0.037 | 0.0075 | 850 |
| B1D.6EO:PPA* (1:1) | 0.037 | 0.0075 | 1000 |

*115% PPA

There is some loss in load bearing capacity by both but those of the present invention are affected to a lesser degree than the commercial product.

The various compounds and mixtures described above will be understood to be by way of exemplification and not by way of limitation.

What is claimed is:

1. Compounds and mixtures of phosphoric acid esters poly(2-10) ethyleneoxy n butane 1,4 diol.

2. Compounds and mixtures of phosphoric acid esters of poly (2-10) ethyleneoxy n butane 1,4 diol as set forth in claim 1 wherein the compounds may be the mono-, di- or triester and the mixtures.

3. Compounds and mixtures of phosphoric acid esters of poly(2-10) ethyleneoxy n butane diol as set forth in claim 1 wherein the monoester is present in a major amount.

4. Compounds and mixtures of phosphoric acid esters of poly(2-10) ethyleneoxy n butane 1,4 diol as set forth in claim 1 wherein the diester is present in a major amount.

5. Compounds and mixtures produced by reacting about 1 mole of n 1,4 butane diol with about 2-10 moles of ethylene oxide, then phosphating the ethoxylated n 1,4 butane diols produced with polyphosphoric acid.

6. Compounds and mixtures produced by reacting about 1 mole of n 1,4 butane diol with about 2-10 moles of ethylene oxide, then posphating the ethoxylated n 1,4 butane diols produced with P$_2$O$_5$.

7. The compounds and mixtures produced as set forth in claim 5 wherein about 6 moles of ethylene oxide are reacted.

8. The compounds and mixtures produced as set forth in claim 6 wherein about 6 moles of ethylene oxide are reacted.

* * * * *